United States Patent [19]
Abraham et al.

[11] Patent Number: 5,753,803
[45] Date of Patent: May 19, 1998

[54] APPARATUS AND METHODS FOR MAINTAINING A SUBSTANTIALLY CONSTANT TEMPERATURE IN A THERMAL PROXIMITY SENSOR

[75] Inventors: David William Abraham, Ossining; Timothy Joseph Chainer, Mahopac; Ferdinand Hendriks, Yorktown Heights, all of N.Y.

[73] Assignee: International Business Machines Corporation, Armonk, N.Y.

[21] Appl. No.: 755,534

[22] Filed: Nov. 21, 1996

[51] Int. Cl.$^6$ .................... G01N 25/72; B23Q 17/09
[52] U.S. Cl. .................. 73/104; 374/5; 374/7; 374/120; 374/137; 374/141; 374/164
[58] Field of Search ................ 374/4, 7, 6, 5, 374/120, 124, 137, 141, 164, 173; 324/721; 73/104, 105

[56] References Cited

U.S. PATENT DOCUMENTS

| | | |
|---|---|---|
| 3,416,373 | 12/1968 | Havens . |
| 3,808,439 | 4/1974 | Renius .................... 374/4 X |
| 4,430,010 | 2/1984 | Zrenner et al. .................... 374/5 X |
| 4,468,136 | 8/1984 | Murphy et al. .................... 374/124 X |
| 4,503,706 | 3/1985 | Kolodjski .................... 73/204 |
| 4,522,510 | 6/1985 | Rosencwaig et al. .................... 374/7 |
| 4,532,802 | 8/1985 | Yeack-Scranton et al. . |
| 4,685,324 | 8/1987 | Bourdon et al. .................... 73/3 |
| 4,747,698 | 5/1988 | Wickramasinghe et al. .................... 374/6 |
| 4,762,427 | 8/1988 | Hori et al. .................... 374/141 |
| 4,853,810 | 8/1989 | Pohl et al. . |
| 4,854,730 | 8/1989 | Fraden .................... 374/164 |
| 4,914,398 | 4/1990 | Jove et al. . |
| 4,931,887 | 6/1990 | Hedge et al. . |
| 5,054,936 | 10/1991 | Fraden .................... 374/164 |
| 5,122,756 | 6/1992 | Nelson .................... 324/720 |
| 5,130,866 | 7/1992 | Klaassen et al. . |
| 5,159,277 | 10/1992 | Mount .................... 324/721 |
| 5,527,110 | 6/1996 | Abraham et al. .................... 374/5 |

FOREIGN PATENT DOCUMENTS 57-30937  2/1982  Japan .................... 324/721

OTHER PUBLICATIONS

"Constant Temperature Anemometry," 20 page handout, Dantec, Date: Prior to Sep. 1995.

*Primary Examiner*—George M. Dombroske
*Assistant Examiner*—Paul D. Amrozowicz
*Attorney, Agent, or Firm*—Heslin & Rothenberg, P.C.

[57] ABSTRACT

Apparatus and methods for improved thermal proximity imaging are provided. A data storage medium surface is moved relative to a sensor, in one embodiment a magnetoresistive read/write element. Topographical variations on the storage medium induce temperature changes in the sensor. These temperature changes are monitored to detect the location and nature (e.g., height) of the topographical variations on the medium surface. A feedback circuit using an impedance bridge is disclosed for sensing instantaneous changes in the temperature of the sensor, correcting for the changes and, therefore, keeping the temperature of the sensor substantially constant. By keeping the temperature of the sensor constant, the topographical variations can be detected without any adverse impacts of the surrounding thermal environment on the detection response time.

10 Claims, 2 Drawing Sheets

APPARATUS AND METHODS FOR MAINTAINING A SUBSTANTIALLY CONSTANT TEMPERATURE IN A THERMAL PROXIMITY SENSOR

RELATED APPLICATION INFORMATION

This application is related to commonly assigned:

U.S. Pat. No. 5,527,110 entitled "Method and Apparatus for Detecting Asperities On Magnetic Disks Using Thermal Proximity Imaging;" and U.S. patent application Ser. No. 08/755,535, entitled "Calibration Apparatus and Methods for a Thermal Proximity Sensor," Attorney Docket No. YO9-96-137, filed concurrently herewith.

This United States patent, and the United States application are hereby incorporated by reference herein in their entirety.

TECHNICAL FIELD

This invention relates generally to apparatus and methods for the detection of topographical variations on a surface of a data storage medium using the thermal response of a sensor moving relative thereto. More particularly, the invention relates to apparatus and methods for maintaining constant the temperature of the sensor used to detect the topographical variations in order to improve the overall response of the sensor.

BACKGROUND OF THE INVENTION

Thermal proximity imaging or sensing is a technique by which topographical variations (e.g., asperities, projections, recesses, etc.) on a data storage medium surface can be detected and characterized by monitoring the thermal response of a sensor in relative motion with the surface. As disclosed in the above-identified U.S. Pat. No. 5,527,110, a sensor, possibly an access element used to read data from or write data to the medium, is heated using a known bias current. The Joule effect heat induced in the sensor by the bias current varies when topographical variations on the surface pass by the sensor during the relative movement between the sensor and the surface. Because the topographical variations vary the distance between the sensor and the surface, and because the heat transferred from the sensor varies as a function of this distance, measuring or monitoring the temperature change of the sensor is a useful technique for identifying the location and character of the topographical variations on the medium.

While a precise understanding of the nature of the heat transfer occurring in and around the sensor as the medium moves relative thereto is yet to be had, it is clear that there is at least some effect on the heat transfer associated with surrounding structures, including shields, insulating materials, etc. Therefore, the response time of this approach is somewhat limited by this heat transfer between the sensor and other surrounding structures. Removing this dependence of the response time on the heat transfer to the surrounding structures is, therefore, required to decrease the overall response time of the system.

Further, the heat transfer and associated temperature changes in the sensor itself have associated therewith a certain amount of thermal lag, such that the response time of the sensor to the topographical variations is somewhat limited.

What is required, therefore, is a technique for thermal proximity imaging which is not limited in response time by the relatively slow heat transfer processes which impact the monitoring of temperature changes in the sensor.

SUMMARY OF THE INVENTION

The above-discussed requirements for a decrease in the response time of a thermal proximity sensor are satisfied by the present invention, which in one aspect is a method for thermally sensing topographical variations on a data storage medium moving relative to, and at a substantially constant distance from, a sensor. Instantaneous changes in a temperature of the sensor are detected. The instantaneous changes are caused by the topographical variations on the data storage medium as the variations move past the sensor. Energy is supplied to the sensor in response to the instantaneous changes in the temperature of the sensor to keep the temperature substantially constant. The energy supplied to the sensor is therefore related to the topographical variations on the data storage medium. The topographical variations can therefore be sensed by monitoring the energy supplied to the sensor in response to the instantaneous changes in the temperature of the sensor.

In an exemplary embodiment, an impedance bridge is used to detect the instantaneous temperature changes, wherein the sensor comprises a first branch of the impedance bridge. Second, third and fourth branches of the bridge comprise known impedances. A feedback element is employed to balance the impedance bridge, a control input of which is driven using a potential of a first node of the impedance bridge. The feedback element drives a second node of the impedance bridge.

In the situation where an inability to balance the impedance bridge occurs, a high temperature interaction between the sensor and the data storage medium can be inferred.

The sensor used for thermal proximity sensing may be a magnetoresistive read element used to read data from the data storage medium.

As discussed in further detail below, by keeping the temperature of the sensor substantially constant, the response time of the system is decreased. The heat transfer to surrounding structures is held constant, and the effect of the thermal lag in the sensor itself is minimized, and therefore the overall response time of the system is improved.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following detailed description of the preferred embodiment(s) and the accompanying drawings in which:

DETAILED DESCRIPTION OF THE PREFERRED EMBODIMENT(S)

Figure 1:
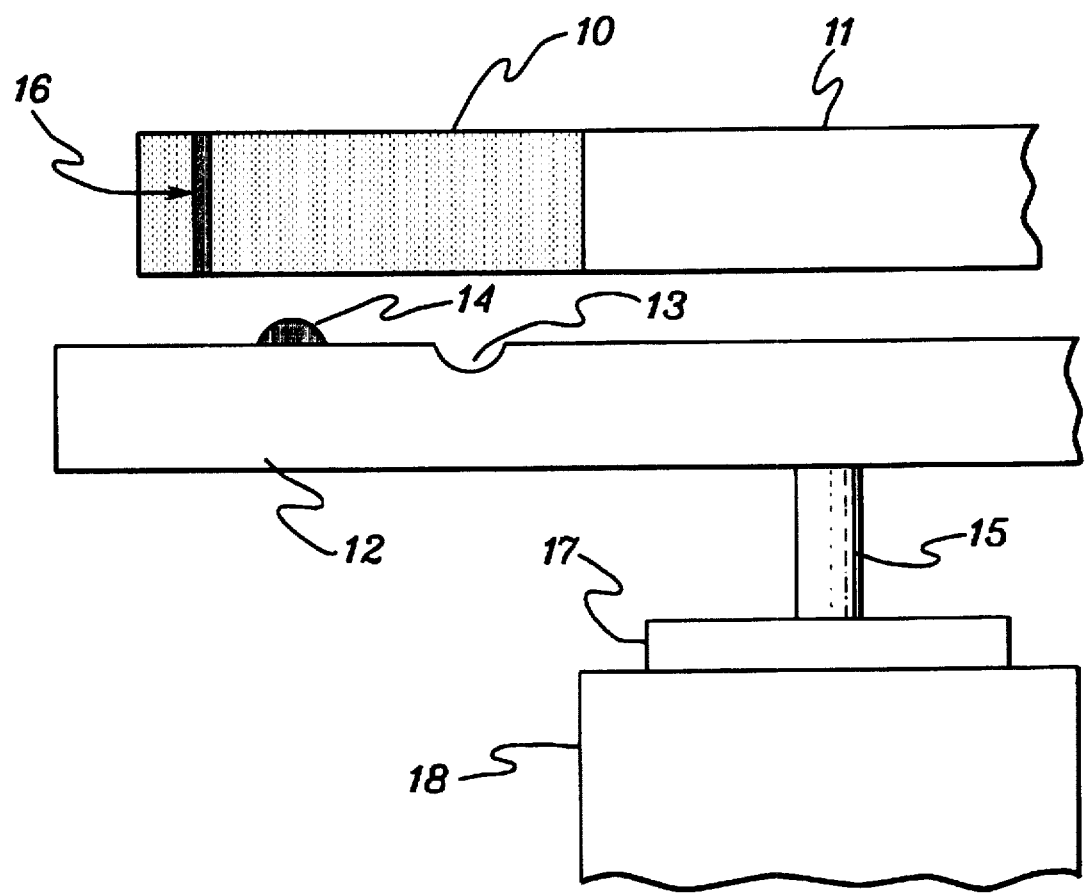
FIG. 1 depicts an exemplary data storage system including a thermal proximity sensing head and a data storage medium having topographical variations thereon.

Referring to the data storage system of FIG. 1, a head including access element 16 on a slider 10 mounted on an actuator 11 is used to sense exemplary topographical variations 13, 14 on a surface of a storage medium 12 (e.g., a disk). Disk 12 rotates on a spindle 15, driven by a motor 18.

(Any type of relative motion between the access element or sensor and the medium is referred to herein as the medium moving relative to the sensor or the sensor moving relative to the medium. This naturally includes a moving medium and fixed sensors, spinning disks, moving tapes, or can be a moving sensor and fixed medium, or any combination thereof.) An encoder 17 provides data on the relative rotational orientation of disk 12 with respect to slider 10.

Slider 10 has an air bearing surface facing disk 12. The relative motion of the air bearing surface of slider 10 and the planar surface of disk 12 maintains a distance between the slider 10 and disk 12 substantially constant. The air bearing surface of slider 10 is designed to provide a constant fly height (for a given rotational disk speed) of slider 10 above the surface of disk 12.

As discussed above, for thermal proximity sensing, the temperature of a sensor, in an embodiment, the exemplary magnetoresistive access element 16, is elevated using Joule heating. As the sensor moves relative to the disk, its instantaneous temperature changes as a function of the instantaneous distance changes between the sensor and the disk. If a protrusion on the surface causes the gap spacing to temporarily vary, or decrease, the temperature will cool and can be sensed as a momentary spike in the electrically monitored thermal response of the sensor signal due to its non-zero temperature co-efficient of resistance. The amplitude of the spike is proportional to the temperature differential maintained in the magnetoresistive element versus the disk surface and to the thermal properties of the protrusion, and depends on the instantaneous sensor-disk spacing (as opposed to the roughly average fly height). This approach, since it depends on temperature changes in the sensor, is affected by the thermal lag in the sensor, and the heat transfer to surrounding structures.

Figure 2:
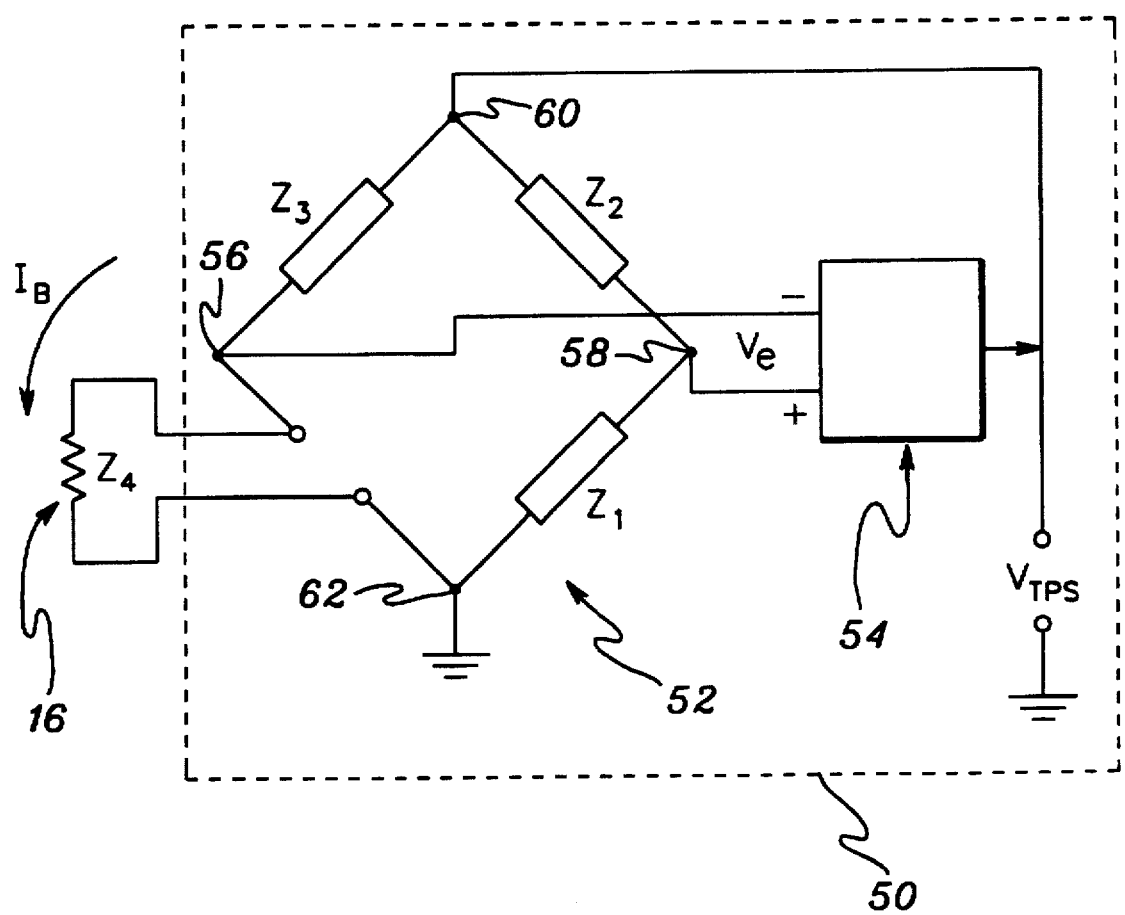
FIG. 2 is a circuit diagram of an exemplary apparatus used to keep the temperature of the thermal proximity sensor constant, in accordance with the principles of the present invention.

In accordance with the instant invention, and with reference to FIG. 2, an electrical control circuit 50 is connected to element or sensor 16 to keep the temperature of sensor 16 substantially constant by varying the bias current $I_B$ supplied thereto in accordance with instantaneous temperature changes detected in the sensor. A feedback element 54 is provided in a feedback configuration, such that an output thereof supplies to the sensor 16 the bias current in accordance with instantaneous temperature changes detected according to a potential difference between nodes 56 and 58. The feedback element may be (without limitation) an energy source such as a simple differential op-amp, but may also include additional proportional integral/differential ("PID") capabilities such that the characteristics of the feedback configuration can be tuned according to the particular nature of the sensor 16.

The overall feedback configuration may include an impedance bridge 52 which, when connected in the depicted configuration, operates to minimize the potential difference $V_e$ between nodes 56 and 58 used as control inputs to supply 54. Impedances $Z_1$, $Z_2$ and $Z_3$ are generally known impedances, chosen to effect bridge operation, considering the range of impedance values that sensor $Z_4$ is expected to exhibit, and the operating bias current $I_B$.

A balance condition exists in impedance bridge 52 when no potential difference exists between nodes 56 and 58 thereof. As the temperature of sensor 16 changes (due to a topographical variation encountered on the associated data storage medium), impedance $Z_4$ changes accordingly. This instantaneous change in $Z_4$ will result in an unbalanced bridge and a potential difference thereby appearing across nodes 56 and 58. In accordance with this potential difference applied as control inputs to feedback element 54, feedback element 54 supplies a voltage across nodes 60 and 62 of the bridge to re-balance the bridge. The bias current $I_B$ has, therefore, been varied in accordance with the instantaneous change in impedance $Z_4$ due to the instantaneous temperature change of sensor 16. Because the Joule heating effect indicates that the temperature of the sensor is related to: the control circuit disclosed in FIG. 2 operates to maintain the temperature of the head substantially constant. $V_{TPS}$ (which corresponds to the voltage output of supply 54) can then be monitored and is representative of the height of the topographical variations encountered on the surface of the medium.

When the temperature changes caused by topographical variations passing the sensor are attributable to normal, spaced flight of the sensor relative to the medium, the disclosed control circuit can be expected to keep the temperature of the sensor substantially constant as discussed above by varying the bias current $I_B$. However, when a high-temperature interaction between the sensor and the surface occurs, such as an impact, the control circuit will be unable to compensate for the excessive temperature changes due to friction, etc. between the surfaces. The inability of the control circuit to compensate can be advantageously used as an indication of such contact, which may in turn indicate a very high protrusion, or some other defect on the surface.

By running at a constant temperature, the temperature profile of the sensor and its surrounding environment remains fixed. Thus, response time limitations associated with the above-discussed exchange of heat from the sensor to the surrounding structures is eliminated. Instead, response time is governed by the electrical feedback loop, and by the time associated only with heat flow from the sensor to the medium itself. Further, by removing the time-dependent heat flow in the sensor, long and short wavelength structures cause the same response in the correction signal in the feedback system. Thermal lag no longer causes a problem, and the resultant data is more directly related to topographical variations on the medium. Naturally, increasing the response time and, therefore, the bandwidth of the sensing system, allows the mapping and characterization of topographical variations to occur with greater precision.

In one example, a typical circular disk moves at 5.400 revolutions per minute, or 90 revolutions per second. An inside diameter radius of 20 mm yields a velocity of about 11.3 meters per second at the inside diameter. A sensing bandwidth of 0.5 MHz without the above-described techniques (corresponding to a 2 microsecond sample rate) yields a resolution of about 23 micrometers. Even a single order of magnitude increase in bandwidth using the instant technique results in a resolution of several micrometers, i.e., a ten-fold improvement.

While the invention has been particularly shown and described with reference to preferred embodiment(s) thereof, it will be understood by those skilled in the art that various changes in form and details may be made therein without departing from the spirit and scope of the invention.

What is claimed is:

1. A method for thermally sensing topographical variations on a data storage medium moving relative to, and at a substantially constant distance from, a sensor, the method comprising:

detecting instantaneous changes in a temperature of the sensor, the instantaneous changes being caused by the topographical variations on the data storage medium as the topographical variations move past the sensor, wherein said detecting instantaneous changes includes using an impedance bridge, the sensor comprising a first branch of the impedance bridge, wherein other branches of the impedance bridge comprise known impedances; and supplying energy to the sensor in response to the instantaneous changes in the temperature of the sensor to keep the temperature of the sensor substantially constant, wherein said supplying energy to the sensor includes balancing the impedance bridge using a feedback element, including driving a control input of the feedback element using a potential of a first node of the impedance bridge, wherein said balancing the impedance bridge using a feedback element includes driving a second node of the bridge with an output of the feedback element, and wherein an inability to balance the impedance bridge using said feedback element indicates a high temperature interaction between the sensor and the data storage medium.

2. The method of claim 1, wherein the high temperature interaction between the sensor and the data storage medium comprises a physical contact between the sensor and the data storage medium, the physical contact thereby being detected based upon the inability to balance the impedance bridge.

3. The method of claim 1, wherein an inability to keep the temperature of the sensor substantially constant indicates a high temperature interaction between the sensor and the data storage medium.

4. The method of claim 3, wherein the high temperature interaction between the sensor and the data storage medium comprises a physical contact between the sensor and the data storage medium.

5. A system for sensing topographical variations on a data storage medium, comprising:

a sensor for mounting in operative relation with the data storage medium, such that upon movement of the data storage medium relative to the sensor a substantially constant distance between the sensor and the data storage medium is maintained; and a control circuit connected to said sensor for supplying energy to said sensor as a function of instantaneous temperature changes of said sensor, the instantaneous temperature changes of said sensor related to instantaneous distance changes between said sensor and the data storage medium and, therefore, related to the topographical variations on the data storage medium, the energy supplied by said control circuit keeping the temperature of said sensor substantially constant, wherein an inability of said control circuit to keep the temperature of said sensor substantially constant is used to indicate a high temperature interaction between said sensor and the data storage medium.

6. The system of claim 5, wherein the high temperature interaction between said sensor and the data storage medium comprises a physical contact therebetween.

7. A system for thermally sensing topographical variations on a data storage medium moving relative to, and at a substantially constant distance from, a sensor, the system comprising:

means for detecting instantaneous changes in a temperature of the sensor, the instantaneous changes being caused by the topographical variations on the data storage medium as the topographical variations move past the sensor, wherein said means for detecting instantaneous changes includes an impedance bridge, the sensor comprising a first branch of the impedance bridge, wherein other branches of the impedance bridge comprise known impedances; and means for supplying energy to the sensor in response to the instantaneous changes in the temperature of the sensor to keep the temperature of the sensor substantially constant, wherein said means for supplying energy to the sensor includes means for balancing the impedance bridge using a feedback element, including means for driving a control input of the feedback element using a potential of a first node of the impedance bridge, wherein said means for balancing the impedance bridge using a feedback element includes means for driving a second node of the bridge with an output of the feedback element, and wherein an inability to balance the impedance bridge using said feedback element indicates a high temperature interaction between the sensor and the data storage medium.

8. The system of claim 7, wherein the high temperature interaction between the sensor and the data storage medium comprises a physical contact between the sensor and the data storage medium, the physical contact thereby being detected based upon the inability to balance the impedance bridge.

9. A system for thermally sensing topographical variations on a data storage medium moving relative to, and at a substantially constant distance from, a sensor, the system comprising:

means for detecting instantaneous changes in a temperature of the sensor, the instantaneous changes being caused by the topographical variations on the data storage medium as the topographical variations move past the sensor; and means for supplying energy to the sensor in response to the instantaneous changes in the temperature of the sensor to keep the temperature of the sensor substantially constant, wherein an inability to keep the temperature of the sensor substantially constant indicates a high temperature interaction between the sensor and the data storage medium.

10. The system of claim 9, wherein the high temperature interaction between the sensor and the data storage medium comprises a physical contact between the sensor and the data storage medium.

* * * * *